United States Patent
Schlomka et al.

(10) Patent No.: US 7,502,437 B2
(45) Date of Patent: Mar. 10, 2009

(54) FOCUSED COHERENT-SCATTER COMPUTER TOMOGRAPHY

(75) Inventors: Jens-Peter Schlomka, Hamburg (DE); Michael Wilhelm Paul Dargatz, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/598,568

(22) PCT Filed: Mar. 1, 2005

(86) PCT No.: PCT/IB2005/050735

§ 371 (c)(1), (2), (4) Date: Sep. 5, 2006

(87) PCT Pub. No.: WO2005/087106

PCT Pub. Date: Sep. 22, 2005

(65) Prior Publication Data

US 2007/0172022 A1    Jul. 26, 2007

(30) Foreign Application Priority Data

Mar. 10, 2004    (EP) ................. 04100980

(51) Int. Cl.
*A61B 6/00*    (2006.01)
*G01N 23/00*    (2006.01)

(52) U.S. Cl. ............................... 378/7; 378/6
(58) Field of Classification Search ................. 378/6–7, 378/148, 4, 19, 86–87
See application file for complete search history.

(56) References Cited

U.S. PATENT DOCUMENTS

| | | | | |
|---|---|---|---|---|
| 4,096,389 A | * | 6/1978 | Ashe et al. | 378/7 |
| 6,175,117 B1 | * | 1/2001 | Komardin et al. | 250/363.06 |
| 6,377,661 B1 | * | 4/2002 | Guru et al. | 378/149 |
| 6,470,067 B1 | * | 10/2002 | Harding | 378/19 |
| 2003/0031295 A1 | * | 2/2003 | Harding | 378/86 |

* cited by examiner

Primary Examiner—Hoon Song (57) ABSTRACT

Due to the provision of slit collimators an intensity of a fan beam is reduced significantly such that expensive high power x-ray tubes have to be used. According to an exemplary embodiment of the present invention, a high power tube may be used with a very long focus in combination with a focusing collimator. The tube can be a cheap fixed anode tube still with a high power of, for example, 15 kW due to the large focus. The collimator may ensure that the resolution of the reconstructed scatter function is not degraded. The illuminated slice thickness is increased which may allow for an isotropic spatial resolution.

14 Claims, 4 Drawing Sheets

FOCUSED COHERENT-SCATTER COMPUTER TOMOGRAPHY

The present invention relates to the field of coherent-scatter computer tomography (CSCT) where a radiation beam is applied to an object of interest. In particular, the present invention relates to a coherent-scatter computer tomography apparatus for examination of an object of interest, to a method of examining an object of interest with a coherent-scatter computer tomography apparatus and to a software program for controlling a computer tomography apparatus.

U.S. Pat. No. 4,751,722 describes a device based on the principle of registration of an angled distribution of coherent scattered radiation within angles of 1° to 12° as related to the direction of the beam. As set forth in the U.S. Pat. No. 4,751,722, the main fraction of elastic scattered radiation is concentrated within angles of less than 12° for photon energies >40 keV, and the scattered radiation has a characteristic angle dependency with well marked maxima, the positions of which are determined by the irradiated substance itself. As the distribution of the intensity of the coherently scattered radiation in small angles depends on molecular structure of the substance, different substances having equal absorption capacity (which cannot be differentiated with conventional transillumination or CT) can be distinguished according to the distribution of the intensity of the angled scattering of coherent radiation typical for each substance.

Due to the improved capabilities of such systems to distinguish different object materials, such systems find more and more application in medical or industrial fields.

The dominant component of low-angle scatter is coherent scatter. Because coherent scatter exhibits interference effects which depend on the atomic arrangement of the scattering sample, coherent scatter computer tomography (CSCT) is in principle a sensitive technique for imaging spatial variations in the molecular structure of tissues or other materials across a 2D object section.

Harding et al "Energy-dispersive x-ray diffraction tomography" Phys. Med. Biol., 1990, Vol. 35, No. 1, 33-41 describes an energy dispersive x-ray diffraction tomograph (EXDT) which is a tomographic imaging technique based on an energy analysis at fixed angle, of coherent x-ray scatter excited in an object by polychromatic radiation. According to this method, a radiation beam is created by the use of suitable aperture systems, which has the form of a pencil and thus is also referred to as a pencil beam. Opposite to the pencil beam source, one detector element suitable for an energy analysis is arranged for detecting the pencil beam altered by the object of interest.

Due to the use of the pencil beam in combination with only one detector element, only a limited number of photons emitted by the source of radiation and thus only a reduced amount of information can be measured. In case EXDT is applied to larger objects such as for example to pieces of baggage, EXDT has to be used in a scanning mode thus causing extremely long measurement times.

A coherent scatter set-up applying a Fan-beam primary beam and a 2D detector in combination with CT was described in U.S. Pat. No. 6,470,067 B1 thus overcoming the long measurement time involved in EXDT scanning mode. The shortcoming of the angle-dispersive set-up in combination with a polychromatic source are blurred scatter functions, which is described in e.g. Schneider et al. "Coherent Scatter Computer Tomography Applying a Fan-Beam Geometry" Proc. SPIE, 2001, Vol. 4320 754-763.

It is an object of the present invention to provide for an improved coherent-scatter computer tomography.

According to an exemplary embodiment of the present invention as set forth in claim 1, the above object may be solved by a coherent-scatter computer tomography apparatus for examination of an object of interest comprising a source of radiation a first radiation detector and a second radiation detector. The source of radiation generates a radiation beam adapted to penetrate the object of interest in a fan plane. The first radiation detector is arranged opposite to the source of radiation in the fan plane. The first radiation detector is arranged to detect a first radiation of the radiation beam transmitted through the object of interest to, for example, thereby detecting an attenuation of the primary radiation by the object of interest. The second radiation detector is arranged opposite to the source of radiation with an offset from the fan plane in a direction which is normal to the fan plane. Thus, the second radiation detector is arranged to detect a second radiation of the radiation beam which is scattered from a location in the object of interest. At the location, according to this exemplary embodiment of the present invention, the radiation beam has a dimension in the direction normal to the fan plane.

According to this exemplary embodiment of the present invention, a scatter angle between photons of the second radiation scattered at the location along the dimension and the fan plane is constant. In other words, the scatter angle of all photons scattered at the location at substantially the whole thickness of the radiation beam is equal for all scatter positions at the location along the dimension i.e. along the "thickness" of the radiation beam at the location. The direction of the 'radiation rays' emitted from the source of radiation and the position of the second radiation detector may be adjusted accordingly.

It has been found that for allowing for a good angle resolution of the system, firstly a fan beam having a very small divergence in the direction normal to the fan plane may be advantageous and secondly, the height of the fan (i.e. the thickness or the dimension of the fan beam in a direction normal to the fan plane) should be small. This may be achieved by using a source of radiation having a very small focal spot and a very narrow slit collimator provided between the source of radiation and the object of interest. For improving the collimation, a second slit may be provided.

However, the collimation by using a slit collimator having one or two slits only allows for the use of source of radiations having relatively small focal spots only. Due to this, high power rotating anodes had to be used to provide for a sufficient flow of photons. The power of such rotating anodes in continuous operation is usually limited to 10-15 kW.

Furthermore, it has been found that the relatively narrow slit causes that only a very small angle of the focus spot is used which further reduces the intensity. This may cause that the thickness of the fan beam is in the area of only 1 mm in the proximity of or in the object of interest. Furthermore, the spatial resolution of CSCT is usually in the range of 5 mm in the fan plane i.e. the resolution is very anisotropic which may cause problems for three-dimensional representations.

The above described deficiencies may advantageously be overcome by the coherent-scatter computer tomography apparatus according to this exemplary embodiment of the present invention where the radiation beam is adapted such the scatter angle between scattered photons of the second radiation and the fan plane is constant.

Furthermore, advantageously, this may allow to achieve a reduced skin dose i.e. a reduced amount of radiation per skin surface. Furthermore, radiation sources, such as x-ray sources, may be used having a large focal spot.

According to another exemplary embodiment of the present invention as set forth in claim 2, the radiation is focused at a focus point having the same distance from the source of radiation as the second radiation detector. According to a variant, the first and second radiation detectors are arranged approximately at the same distance from the location of the focal spot. I.e. the first and second radiation detectors are arranged at a circular path of a circle with the same radius in the fan-plane having its center at the location of the X-ray source, i.e. the positions of the first and second radiation detector only differ by a distance along the axis of rotation.

According to another exemplary embodiment of the present invention as set forth in claim 3, a collimator is arranged between the object of interest and the source of radiation which is adapted to collimate the radiation beam such that it is focused at a distance from the source which is equal to the distance between the second radiation detector and the source. Advantageously, the first detector is placed at the focus position such that the primary radiation detector measures the attenuation of the primary radiation at its path through the object of interest.

Advantageously, this may allow to have a fan beam having at the location of the object of interest an enlarged thickness i.e. enlarged dimensions along a direction perpendicular or normal to the fan plane. Due to this, a surface of the body where the radiation enters the body of the object of interest is enlarged which allows for reduced skin dose. Also, this allows for the use of sources of radiation having an enlarged focal spot. Also, due to the collimation onto the center line of the detector, advantageously, it may be achieved that the scatter angle between photons of the second radiation scatter that the location along the dimension and the fan plane is constant.

According to another exemplary embodiment of the present invention as set forth in claim 4, the collimator may be realized by a plurality of tungsten or molybdenum sheets and the plurality of tapered plastic layers sandwiched between the tungsten sheets. Also non-tapered plastic layers can be used and the focusing can be achieved by applying mechanical pressure onto one side of the collimator.

Advantageously, this may allow for the provision of a collimator having a simple arrangement. As plastic layers, according to a variant of this exemplary embodiment, a plastic foam may be used. The layers may also consist of holes (like a cheese) or be put together from discrete strips of material.

According to another exemplary embodiment of the present invention as set forth in claim 5, the first and second detectors are realized as detector lines each line being arranged in parallel to the fan plane.

According to another exemplary embodiment of the present invention as set forth in claim 6, a method of examining an object of interest with a coherent-scatter computer tomography apparatus is provided wherein the scatter angle is constant.

Advantageously, the method according to this exemplary embodiment of the present invention may allow to avoid problems in three-dimensional representation due to the fact that the resolution has a reduced anisotropy.

According to another exemplary embodiment of the present invention as set forth in claim 7, the radiation beam is collimated such that it is focused at the primary radiation detector i.e. the transmission detector.

According to another exemplary embodiment of the present invention as set forth in claim 8, a software program for controlling a computer tomography apparatus is provided wherein, when the software is executed on a processor of the computer tomography apparatus, the computer tomography apparatus performs an operation in accordance with the method of the present invention. The computer program according to the present invention may be stored on a computer readable medium, such as a CD-ROM. The computer program may also be presented of a network, such as the WorldWideWeb and may be downloaded into the working memory of a data processor from such a network. The computer program may be written in any suitable programming language, such as C++.

It may be seen as a gist of an exemplary embodiment of the present invention that the radiation beam is formed such that it is focused at a distance from the focal spot which is equal to the distance between the scatter detector and the focal spot. The scattered photons may have their focus at the scatter radiation detector and the scatter angle is constant. According to an exemplary embodiment of the present invention, this may be realized by means of a focusing collimator which focuses the radiation beam onto the transmission radiation detector.

These and other aspects of the present invention are apparent from and will be elucidated with reference to the embodiments described hereinafter and with reference to the following drawings.

In the following description of FIGS. 1-7, the same reference numerals will be used for the same or corresponding elements.

Figure 1:
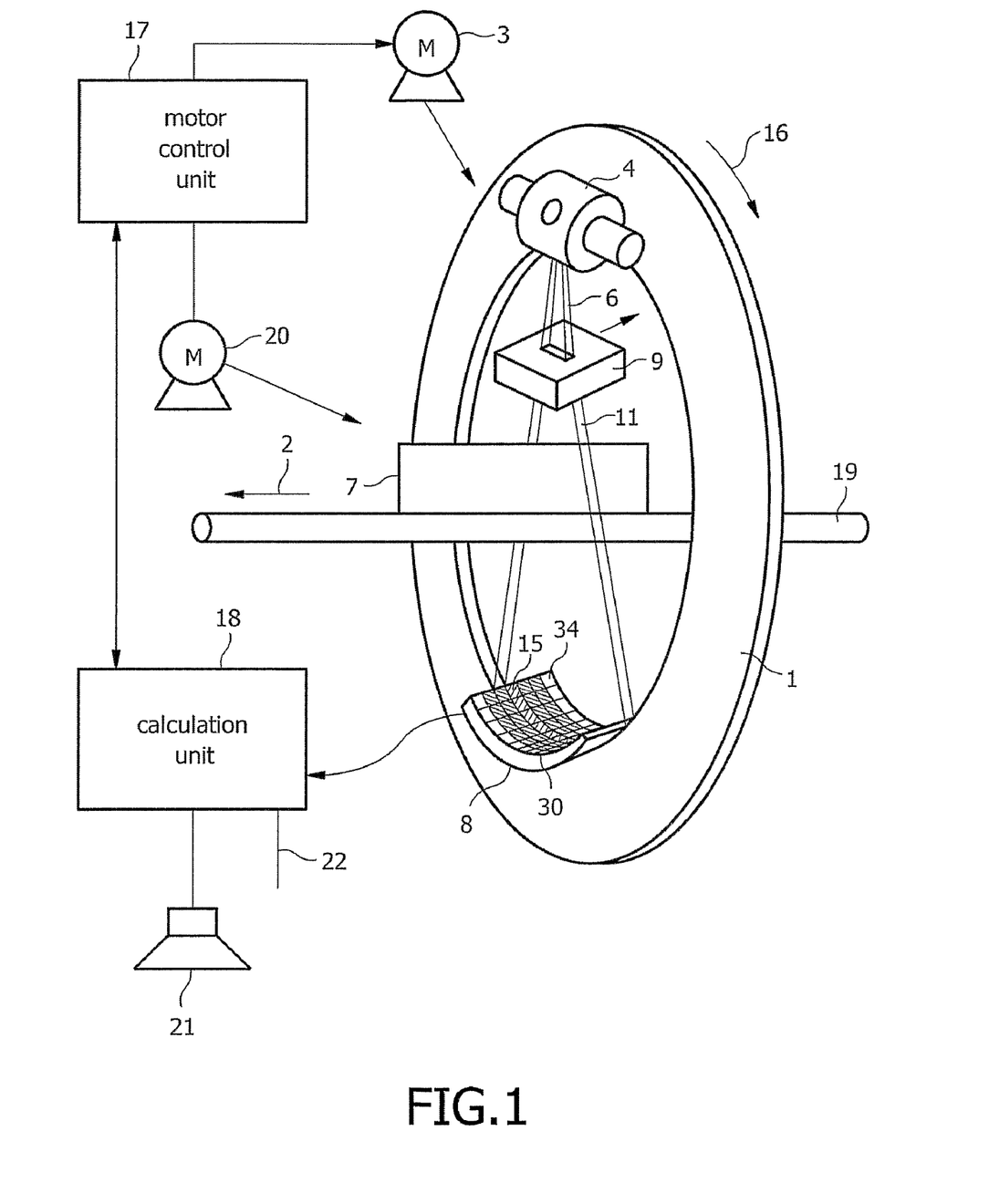
FIG. 1 shows a schematic representation of an exemplary embodiment of a computer-tomograph according to the present invention.

FIG. 1 shows an exemplary embodiment of a computer-tomograph according to the present invention. With reference to this exemplary embodiment, the present invention will be described for the application in baggage inspection, for example to detect hazardous materials, such as explosives, in items of baggage. However, it has to be noted that the present invention is not limited to the fields of baggage inspection, but can also be used in other industrial or medical applications, such as, for example, in bone imaging or discrimination of tissue types in medical applications.

The computer-tomograph depicted in FIG. 1 is a fan beam coherent-scatter computer-tomograph (CSCT) which allows the use of a source of radiation for having an enlarged focal spot. Furthermore, according to an exemplary embodiment of the present invention, no high performance rotating anode need to be used for providing a sufficiently high photon flow. The arrangement of the source of radiation 4 will be described in further detail with respect to FIG. 6.

The computer-tomograph depicted in FIG. 1 comprises a gantry 1, which is rotatable around a rotational axis 2. The gantry 1 is driven by means of a motor 3. Reference character 4 designates the source of radiation, such as an x-ray source which, according to an aspect of the present invention emits polychromatic or monochromatic radiation.

Reference numeral 9 designates a collimator. The collimator according to this exemplary embodiment of the present invention is arranged such that it forms a beam of radiation 6 such that the rays of the radiation beam 6 are focused on a transmission detector line 15 of a radiation detector 8 arranged at the gantry 1 opposite to the source of radiation 4. The transmission detector line 15 of fan beam 11 penetrating through the object of interest 7 intersects the transmission detector line 15 of the radiation detector 8 in the fan plane.

In other words, the fan beam 11 is directed such that it penetrates the item of baggage 7 arranged in the center of the gantry 1 i.e. in an examination region of the computer-tomograph and impinges onto the detector 8. As described above, the detector 8 is arranged on the gantry 1 opposite to the radiation source 4 such that the fan plane of the fan beam 11 intersects the row or line 15 of the detector 8. The detector 8 is depicted in FIG. 1 as having seven detector lines, each comprising a plurality of detector elements. As mentioned above, the detector 8 is arranged such that the primary radiation detector 15 i.e. the middle line of the detector 8 is in the fan plane of the fan beam 11.

The remaining six lines of the detector 8 i.e. the three detector lines 30 and 34 on each side of the detector line 15 indicated with hatching are scatter radiation detector lines. Such detector lines 30 and 34 are respectively arranged outside of the fan plane of the fan beam 11. In other words, those lines 30 and 34 are arranged at the gantry 1 opposite to the x-ray source 4 with an offset from the fan plane in a direction parallel to the rotational axis 2 or in a direction normal to the fan plane. The detector line 30 is arranged with a positive offset with respect to the direction of the rotational axis 2 depicted in FIG. 1 whereas the line 34 is arranged with a negative offset from the fan plane with respect to the direction of the rotational axis 2 depicted in FIG. 1.

The detector lines 30 and 34 arranged at the gantry 1 such that they are parallel to the fan plane and out of the fan plane with such an offset in a positive or negative direction of the rotational axis 2 of the gantry 1 such that they receive or measure a scatter radiation scattered from the item of baggage 7 in the examination area of the computer-tomograph. Thus, in the following, lines 30 and 34 will also be referred to a scatter radiation detector.

The detector elements of the detector lines 15, 30 and 34 may be scintillator detector cells. However, according to a variant of this exemplary embodiment of the present invention cadmium telluride or CdZnTe based or other direct-conversion detector cells may be used for either line 15 or line 34 or 30. Also, lines 30 and 34 may be cadmium telluride or CZT based detector cells and the line 15 may be a scintillator detector cell. The primary beam detectors and the scatter radiation detectors may be placed in separate housings.

It has to be noted that the provision of only one line 30 or 34 may be sufficient. However, preferably a plurality of lines 30 and/or 34 are provided. Also, the provision of only one line 15 measuring the attenuation caused by the item of baggage 7 of the primary beam of the fan beam 11 in the fan plane may be sufficient. However, as in the case of the lines 30 and 34, a provision of a plurality of detector lines 15 may further increase the measurement speed of the computer-tomograph. In the following, the term "primary radiation detector" will be used to refer to a detector, including at least one detector line for measuring an attenuation of the primary radiation of the fan beam 11.

As may be taken from FIG. 1, the detector cells of the detector 8 are arranged in lines and columns, wherein the columns are parallel to the rotational axis 2, wherein the lines are arranged in planes perpendicular to the rotational axis 2 and parallel to the slice plane of the fan beam 11.

During a scan of the item of baggage 7, the radiation source 4, the aperture system i.e. the collimator 9 and the detector 8 are rotated along the gantry 1 in the direction indicated with arrow 16. For rotation of the gantry 1 the motor 3 is connected to a motor control unit 17, which is connected to a calculation unit 18.

In FIG. 1, the item of baggage 7 is disposed on a conveyor belt 19. During the scan of the item of baggage 7, while the gantry 1 rotates around the item of baggage 7, the conveyor belt 19 displaces the item of baggage 7 along a direction parallel to the rotational axis 2 of the gantry 1. By this, the item of baggage 7 is scanned along a helical scan path. The conveyor belt 19 can also be stopped during the scans to thereby measure single slices.

The detector 8 is connected to a calculation unit 18. The calculation unit 18 receives the detection results, i.e. the readouts from the detector elements of the detector 8 and determines a scanning result on the basis of the scanning results from the detector 8, i.e. from the energy resolving lines 30 and 34 and the line 15 for measuring the attenuation of the primary radiation of the fan-beam 11. In addition to that, the calculation unit 18 communicates with the motor control unit 17 in order to coordinate the movement of the gantry 1 with the motors 3 and 20 or with the conveyor belt 19.

The calculation unit 18 is adapted for reconstructing an image from readouts of the primary radiation detector, i.e. Detector line 15 and the scatter radiation detector, i.e. lines 30 and 34. The image generated by the calculation unit 18 may be output to a display (not shown in FIG. 1) via an interface 22.

Furthermore, the calculation unit 18 is adapted for the detection of explosives in the item of baggage 7 on the basis of the readouts of the lines 30 and 34 and 15 and 32. This can be made automatically by reconstructing scatter functions from the readouts of these detector lines and comparing them to tables including characteristic measurement values of explosives determined during preceding measurements. In case the calculation unit 18 determines that the measurement values read out from the detector 8 match with characteristic measurement values of an explosive, the calculation unit 18 automatically outputs an alarm via a loudspeaker 21.

Figure 2:
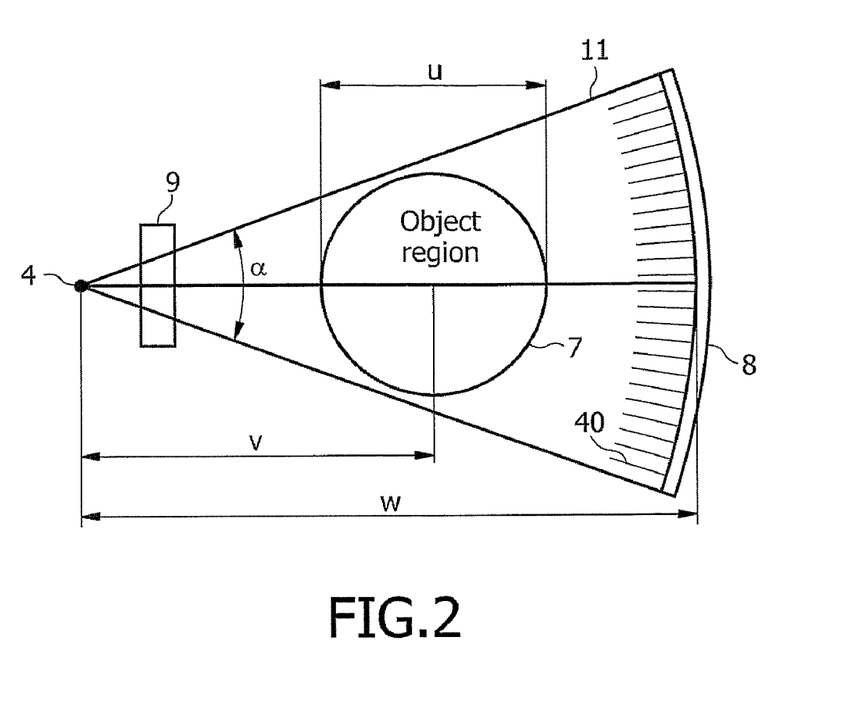
FIG. 2 shows a schematic representation of the geometry of the computer-tomograph of FIG. 1 for the measurement of coherent-scatter radiation.

FIG. 2 shows a simplified schematic representation of a geometry of the CSCT scanning system depicted in FIG. 1. As may be taken from FIG. 2, the x-ray source 4 emits the fan-beam 11 such that it includes the item of baggage 7 in this case having a diameter of u and covers the entire detector 8. The diameter of the object region may, for example, be 100 cm. In this case, an angle α of the fan-beam 11 may be 80°. In such an arrangement, a distance v from the x-ray source 4 to the center of the object region is approximately 80 cm and the distance of the detector 8, i.e. of the individual detector cells from the x-ray source 4 is approximately w=150 cm.

As can be taken from FIG. 2, according to an aspect of the present invention, the detector cells or lines can be provided with collimators 40 to avoid that the cells or lines measure unwanted radiation having a different scatter angle. The collimators 40 have the form of blades or lamellas, which can be focused towards the source. The spacing of the lamellas can be chosen independently from the spacing of the detector elements.

Instead of a bent detector 8 as depicted in FIGS. 1 and 2, it is also possible to use a flat detector array.

Figure 3:
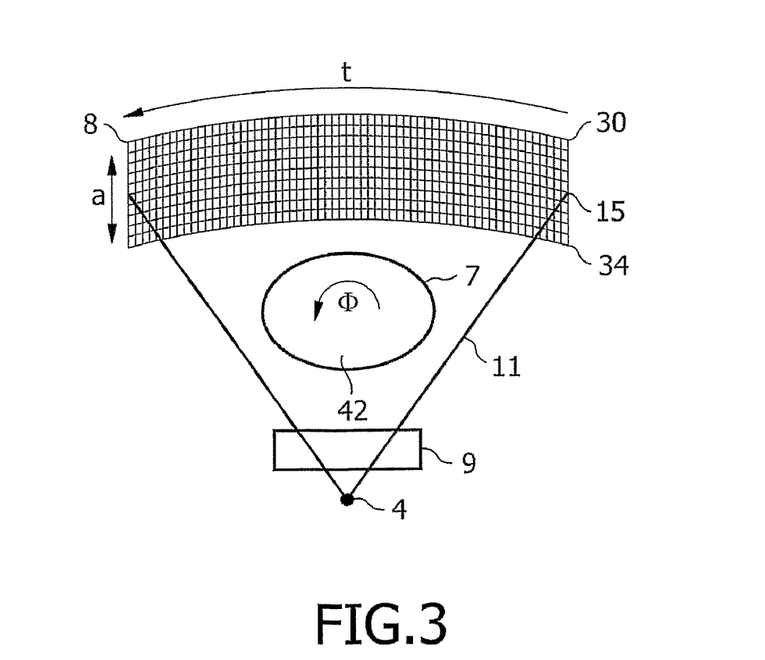
FIG. 3 shows another schematic representation of the geometry of the computer-tomograph of FIG. 1.

FIG. 3 shows another schematic representation of a detector geometry as used in the computer tomograph of FIG. 1. As already described with reference to FIG. 1, the detector 8 may comprise one, two or more detector lines 30 and 34 and a plurality of lines 15 for measuring the attenuation of the primary fan-beam caused by the item of baggage 7. As may be taken from FIG. 3, preferably the detector 8 is arranged such that the middle line 15 of the detector 8, is within the fan plane of the fan-beam 11 and thereby measures the attenuation in the primary radiation. As indicated by arrow 42, the radiation source of x-ray source 4 and the detector 8 are rotated together around the item of baggage to acquire projections from different angles.

As depicted in FIG. 3, the detector 8 comprises a plurality of columns t.

Figure 4:
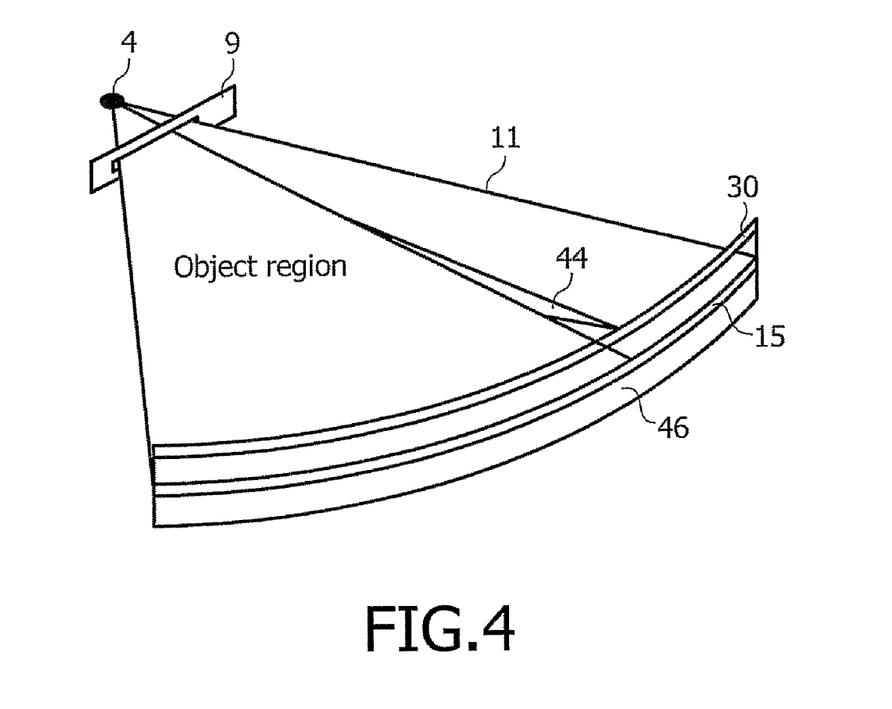
FIG. 4 shows another schematic representation of the measurement geometry of the computer-tomograph of FIG. 1 for further explaining the present invention.

FIG. 4 shows another schematic representation of the geometry of the computer tomograph depicted in FIG. 1 for further explaining the present invention. In FIG. 4, a detector 46 is depicted, comprising only one line 15 and only one line 30. The line 15 is arranged in the fan plane of the fan-beam 11 formed by the collimator 9. The line 15 comprises, for example, scintillator cells or other suitable cells for measuring the attenuation of the primary beam of the fan-beam 11 and allows for an integral measurement of the attenuation of the primary fan-beam caused by the object of interest in the object region or examination region.

Line 30 depicted in FIG. 4 may include energy resolving cells or scintillator cells. As may be taken from FIG. 4, the line 30 is arranged parallel to the fan plane of the fan-beam 11 but out of the plane. In other words, the line 30 is arranged in a plane parallel to the fan plane and parallel to the line 15. The fan plane may also be referred to as slice plane.

Reference numeral 44 indicates a scatter radiation, i.e. a photon scattered by the object of interest, such as the item of baggage. As may be taken from FIG. 4, the scatter radiation leaves the slice plane and impinges onto a detector cell of the line 30.

Figure 5:
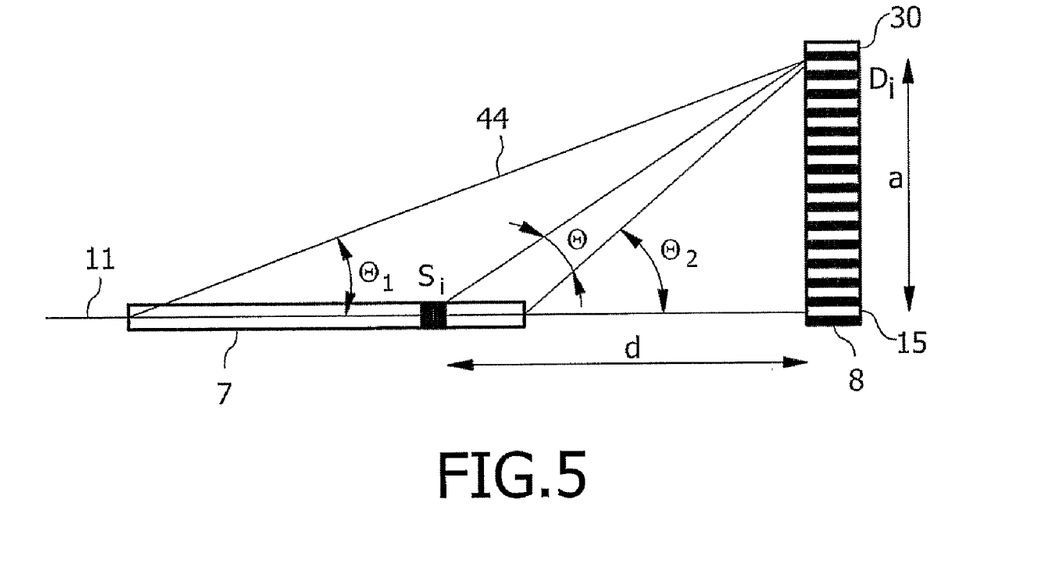
FIG. 5 shows a schematic representation of a side view of the geometry of the computer-tomograph of FIG. 1.

FIG. 5 shows a side view of the detector geometry of the computer tomograph of FIG. 1. FIG. 5 can also be contemplated as showing a side view of FIG. 4, where, however, instead only the provision of one line 30 and one line 15, in FIG. 5, there is provided a plurality of detector lines 32 between the line 30 and the line 15. The detector element $D_i$ is arranged with a fixed distance a from the slice plane of the primary fan-beam. According to an aspect of the present invention, for each detector element $D_i$ of the column t and for each projection $\Phi$ (see FIG. 3) a spectrum I (E, t, $\Phi$) is measured. Performing this measurement for a plurality of projections $\Phi$ along a circular or helical scan path, a three-dimensional dataset is acquired. Each object pixel is described by three coordinates (x, y, q). Thus, according to an aspect of the present invention, for reconstructing an image or for reconstructing further information from the three-dimensional dataset, a 3D→3D reconstruction method such as the one described in DE 10252662.1, which is hereby incorporated by reference.

On the basis of the spatial coordinates (x, y), a distance d of each object voxel $S_i$ to the detector 8 is calculated by means of the calculation unit 18. Then, the calculation unit 18 calculates a scatter angle θ for each object voxel $S_i$ and spaces of the following equation:

$$\theta = a\tan(a/d)$$ (Equation 1).

Then, on the basis of this calculation, the calculation unit 18 calculates the wave-vector transfer parameter q on the basis of the following equation:

$$q = \frac{E}{hc}\sin(\theta/2),$$ (Equation 2)

wherein h is the Planck's constant and c is the speed of light and E the photon energy.

Then, on the basis of the wave-vector transfer parameter q calculated in accordance with the above formula and on the basis of the readouts of the primary radiation detector, the calculation unit 18 may determine an image or may discriminate the material in the object slice.

Figure 6:
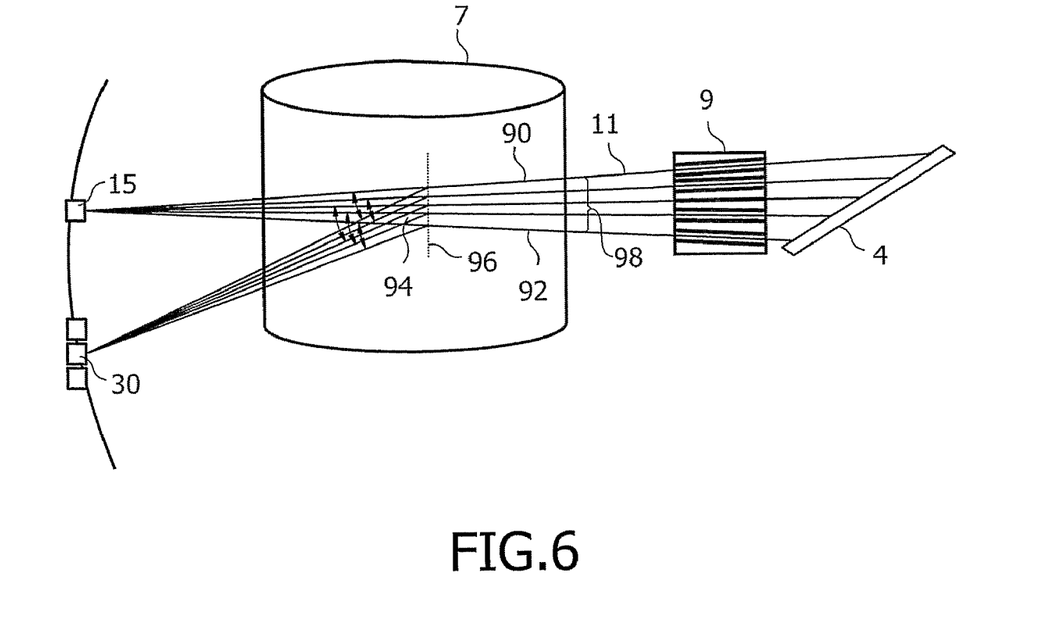
FIG. 6 shows another side view of a computer-tomograph according to the present invention.

FIG. 6 shows a side view of an exemplary embodiment of a computer tomography apparatus according to the present invention. As may be taken from FIG. 6, the item of baggage 7 or the object of interest or the patient is arranged between detector lines 15 and 30 on one side and the collimator 9 and the source of radiation 4 on the other side. The perspective in FIG. 6 is essentially the same perspective as FIG. 5.

The radiation source 4 depicted in FIG. 6 has a focal spot which has normally a limited extension into the fan plane i.e. into the paper in accordance with perspective shown in FIG. 6. A relatively small dimension into the fan plane may be in the range from 0.5 mm-8 mm. Essentially, the extension may be in the range of 3 mm.

However, as may be taken from FIG. 6, the dimension of the source of radiation 4 in a direction perpendicular to the fan plane may be substantial. For example, a focal spot i.e. a spot of the source of radiation 4 where radiation is emitted may have a dimension of 10 mm or more in a direction perpendicular to the fan plane.

As may be taken from FIG. 6, the focal spot of the source of radiation 4 may be inclined with respect to the fan plane. For example, the inclination may be between 7° and 20°. However, also smaller or larger inclinations may be used.

By using a source of radiation 4 having a focal spot with a relatively small extension in a direction parallel to the fan plane and by inclining the source of radiation 4 such that the focal spot of the source of radiation 4 is inclined with respect to the fan plane a punctiform focal spot may be realized with respect to detector line 15. In other words, if it is looked upon the source of radiation 4 from the detector line 15, a punctiform or punctual focal spot of the source of radiation 4 can be seen.

Thus, for example, by using a source of radiation 4 having a focal spot extending 2 mm parallel to the fan plane and 10 mm perpendicular to the fan plane and contemplating an inclination of 22°, a true focal spot size of 2 mm×(10/sin 20°)mm=58.5 $mm^2$ may be realized. Having such a large focal spot, source of radiations having a fixed anode may be used. Also, more than 15 kW may be realized.

As may be taken from FIG. 6, the radiation emitted from the source of radiation 4 is collimated by means of collimator 9 which will be described in further detail with reference to FIG. 7. According to another exemplary embodiment of the present invention, the collimator 9 is arranged such that the radiation is focused onto the detector line 15 i.e. onto the transmission radiation detector or primary radiation detector. As may be seen from FIG. 6, the fan beam 11 collimated by means of the collimator 9 has an extension in a direction perpendicular to the fan plane. According to the present invention, such an extension may be in the range of 0.5-3 or 4 mm. However, such an extension may also be up to 10 or 12 mm. Due to this, a surface 98 of the item of baggage 7 or the object of interest such as a patient where the radiation enters into the object of interest is enlarged. This may advantageously allow to reduce a skin dose i.e. the amount of radiation applied to the surface of the object of interest such as the patient.

At a location in the object of interest 7 indicated by line 96 radiation is scattered from the fan beam 11. Such radiation which is referred to a scatter radiation in the following is focused onto scatter radiation detector line 30. According to an exemplary embodiment of the present invention the scatter radiation i.e. Detector line 30 is arranged at a location such that a scatter angle 94 of the respective photons scattered at the location indicated by line 96 is the same for all photons of the fan beam 11 scattered at the location indicated by line 96. In other words, the photon scattered along a ray 90 is scattered towards the radiation detector line 30 with the same angle to the fan plane as the photon of ray 92.

In other words, according to this exemplary embodiment of the present invention, the radiation is collimated through a focusing collimator 9. The focus line of the collimator 9 is the primary detector line 15.

When the focused fan beam 11 is scattered at a location in the object of interest and the scatter radiation is detected by one or more scatter radiation detectors 30, the scatter angle is independent of the height of the scattering along line 96. I.e. the scatter angle is independent for all scatter incidents occurring in fan beam 11 along line 96. This may be allowed by the fact that a distance between the source of radiation and the primary radiation detector 15 is the same as the distance between the scatter radiation detector and the source of radiation 4. Also, it may be sufficient to arrange the second radiation detector at the same distance from the source of radiation and to arrange the first radiation detector out of focus, i.e. closer or more distant.

Such arrangement may be approximated when a cylindrical CT detector is used and a distance between the object of interest and the detector is sufficiently large.

As already indicated above, the height of the fan at the incident into the body is enlarged which allows for distributing the skin dose over a larger surface. By this, according to the present invention, a skin dose may be reduced by a factor of 5 contemplating the same amount of scattered photons on the detector without degeneration of the quality of the scatter spectrum.

Figure 7:
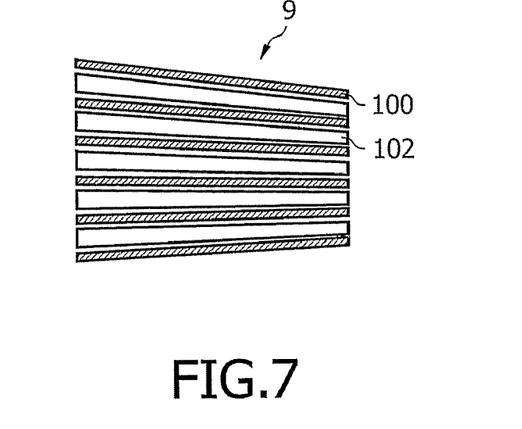
FIG. 7 shows the cross-sectional view of an exemplary embodiment of a focusing collimator according to the present invention as it may be used in the computer-tomograph of FIG. 6.

FIG. 7 shows a cross-sectional view of the collimator 9. As may be taken from FIG. 7, the collimator 9 comprises a plurality of layers having an inclination with respect to each other. According to this exemplary embodiment of the present invention, the collimator 9 comprises a plurality of layers 100 made of tungsten or molybdenum material which are very strong absorbing with respect to the radiation. Furthermore, between the layers 100 there are provided layers 102 which are made of non- or almost non-absorbing materials. For example, as material for the layers 100, tungsten may be used for layers 102, plastic or a plastic foam such as PU foam or a material named "Rohacell" (Polymethacrylimid foam) may be used. The layers 102 may be tapered or the focusing may be achieved by applying mechanical pressure from top and bottom onto the left side of the collimator.

As may be taken from FIG. 6, the layers are packed very tightly and have a length such that a divergence of the fan beam 11 out of the fan plane is relatively small, for example in the range of 0.1°-0.3°.

Advantageously, the above described present invention may allow for the use of relatively cheap fixed anode tubes having a high power of, for example, 15 kW. This may be realized due to the large focus allowed for by the present invention. Also, the inclination of the source of radiation may allow for an enlarged focal spot. Due to the enlarged thickness of the fan plane, an isotropic resolution of the CSCT scanner may be realized. Furthermore, as already been described above, the skin dose may be reduced significantly.

The invention claimed is:

1. Coherent scatter computer tomography apparatus for examination of an object of interest, comprising:
   a source of radiation;
   a first radiation detector; and
   a second radiation detector; wherein the source of radiation generates a radiation beam adapted to penetrate the object of interest in a fan plane and wherein the source of radiation is inclined with respect to the fan plane; wherein the coherent scatter computer tomography apparatus further comprises a collimator arranged between the source of radiation and the object of interest, wherein the collimator comprises a plurality of collimator portions that collimate the radiation beam in a direction substantially perpendicular to the fan plane, wherein the first radiation detector is arranged opposite to the source of radiation in the fane plane; wherein the first radiation detector is arranged to detect a first radiation of the collimated radiation beam; wherein the second radiation detector is arranged opposite to the source of radiation with an offset from the fan plane in a direction normal to the fan plane; wherein the second radiation detector is arranged to detect a second radiation of the collimated radiation beam scattered from a location in the object of interest; wherein at the location, the second radiation has a dimension in the direction normal to the fan plane; wherein a scatter angle between photons of the second radiation scattered at the location along the dimension from the fan plane is constant.

2. The coherent scatter computer tomography apparatus of claim 1, wherein the radiation beam is focused at a focus point by the collimator; wherein the focus point is at a distance from the source of radiation; and wherein the second radiation detector is arranged at the distance from the source of radiation.

3. The coherent scatter computer tomography apparatus of claim 1, wherein the collimator is adapted to collimate the radiation beam such that the radiation beam is focused at a focus point being at the same distance form the source of radiation as the second radiation detector.

4. The coherent scatter computer tomography apparatus of claim 3, wherein the collimator comprises a first plurality of high-Z material sheets and a second plurality of tapered plastic layers sandwiched between the first plurality of high-Z material sheets, wherein each of the first plurality of high-Z material sheets and each of the second plurality of tapered plastic layers have an inclination with respect to each other of the first plurality of high-Z material sheets and other each of the second plurality of tapered plastic layers.

5. The coherent scatter computer tomography apparatus of claim 3, wherein the collimator comprises a first plurality of high-Z material sheets and a second plurality of plastic layers sandwiched between the first plurality of high-Z material sheets; wherein the focusing of the radiation beam at the focus point is performed by deforming the plastic layers by applying inhomogeneous mechanical pressure onto the collimator such that each of the first plurality of high-Z material sheets and each of the second plurality of tapered plastic layers have an inclination with respect to each other of the first plurality of high-Z material sheets and other each of the second plurality of tapered plastic layers.

6. The coherent scatter computer tomography apparatus of claim 1, wherein each of the first and second detectors comprises a line of detector elements, each of these lines being arranged in parallel to the fan plane.

7. A method of examining an object of interest with a coherent scatter computer tomography apparatus, the method comprising the acts of:
generating a radiation beam penetrating the object of interest in a fan plane, wherein the radiation beam is generated as stacked collimated beams that are stacked in a direction substantially perpendicular to the fan plan and wherein a source of the radiation beam is inclined with respect to the fan plane;
detecting a first radiation of the radiation beam transmitted through the object of interest;
detecting a second radiation of the radiation beam scattered from a location in the object of interest; wherein the location has an offset from the fan plane in a direction normal to the fan plane; wherein at the location, the second radiation has a dimension in the direction normal to the fan plane; wherein the radiation beam is generated such that a scatter angle between photons of the second radiation scattered at the location along the dimension from the fan plane is constant.

8. The method of claim 7, wherein the collimated beams are focused at a focus point having the same distance from a source of radiation as a point where the second radiation is detected.

9. A software program stored on a computer-readable medium for controlling a computer tomography apparatus, wherein, when the software is executed on a processor of the computer tomography apparatus, the computer tomography apparatus performs the following operation:
generating a radiation beam penetrating the object of interest in a fan plane, wherein the radiation beam is generated as stacked collimated beams that are stacked in a direction substantially perpendicular to the fan plan and wherein a source of the radiation beam is inclined with respect to the fan plane;
detecting a first radiation of the radiation beam transmitted through the object of interest;
detecting a second radiation of the radiation beam scattered from a location in the object of interest; wherein the location has an offset from the fan plane in a direction normal to the fan plane; wherein at the location, the second radiation has a dimension in the direction normal to the fan plane; wherein the radiation beam is generated such that a scatter angle between photons of the second radiation scattered at the location along the dimension from the fan plane is constant.

10. The coherent scatter computer tomography apparatus of claim 4, wherein the second plurality of tapered plastic layers form tapers that vary with respect to each other such that a beam path through one of the collimator portions varies in length with respect to another one of the collimator portions.

11. The coherent scatter computer tomography apparatus of claim 1, wherein the second radiation detector is portion of a flat radiation detector.

12. The coherent scatter computer tomography apparatus of claim 1, comprising a table of reconstruction scatter functions, wherein the coherent scatter computer tomography apparatus is configured to determine a scatter function from the detected first and second radiation and is configured to compare the determined scatter function to the table of reconstruction scatter functions.

13. The method of claim 7 comprising an act of providing a collimator arranged between the source of radiation and the object of interest, wherein the collimator comprises a plurality of collimator portions that inclined with respect to each other and that collimate the radiation beam in a direction substantially perpendicular to the fan plane.

14. The method of claim 7, comprising an acts of:
determining a scatter function from the detected first and second radiation; and
comparing the determined scatter function to a table of reconstruction scatter functions.

* * * * *